US008740751B2

(12) United States Patent
Shum (10) Patent No.: US 8,740,751 B2
(45) Date of Patent: Jun. 3, 2014

(54) INTERFACES AND SYSTEMS FOR DISPLAYING ATHLETIC PERFORMANCE INFORMATION ON ELECTRONIC DEVICES

(75) Inventor: Albert Shum, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 894 days.

(21) Appl. No.: 11/188,112

(22) Filed: Jul. 25, 2005

(65) Prior Publication Data

US 2007/0021269 A1 Jan. 25, 2007

(51) Int. Cl.
*A63B 71/00* (2006.01)
(52) U.S. Cl.
USPC .................................... 482/8; 482/1
(58) Field of Classification Search
USPC .................... 482/1–9; 702/182, 96
See application file for complete search history.

(56) References Cited

U.S. PATENT DOCUMENTS

| | | | |
|---|---|---|---|
| 5,335,188 A | 8/1994 | Brisson | |
| 5,596,652 A | 1/1997 | Piatek et al. | |
| 5,598,849 A | 2/1997 | Browne | |
| 5,793,882 A | 8/1998 | Piatek et al. | |
| 5,890,997 A | 4/1999 | Roth | |
| 5,931,763 A | 8/1999 | Alessandri | |
| 6,013,007 A | 1/2000 | Root et al. | |
| 6,077,193 A | 6/2000 | Buhler et al. | |
| 6,375,612 B1 | 4/2002 | Guichon et al. | |
| 6,396,413 B2 | 5/2002 | Hines et al. | |
| 6,424,264 B1 | 7/2002 | Giraldin et al. | |
| 6,463,385 B1 | 10/2002 | Fry | |
| 6,526,158 B1 | 2/2003 | Goldberg | |
| 6,531,963 B1 | 3/2003 | Nyfelt | |
| 6,569,092 B1 | 5/2003 | Guichon et al. | |
| 6,600,407 B2 | 7/2003 | Paek | |
| 6,614,392 B2 | 9/2003 | Howard | |
| 6,898,550 B1 * | 5/2005 | Blackadar et al. ............ 702/182 |
| 7,101,287 B1 | 9/2006 | Wagner | |
| 7,254,516 B2 * | 8/2007 | Case et al. .................... 702/182 |
| 2001/0054014 A1 | 12/2001 | Noda et al. | |
| 2002/0022551 A1 | 2/2002 | Watterson et al. | |

(Continued)

FOREIGN PATENT DOCUMENTS

| | | |
|---|---|---|
| EP | 1134555 A1 | 9/2001 |
| JP | 2002-541937 A | 12/2002 |

(Continued)

OTHER PUBLICATIONS

International Search Report dated Apr. 23, 2007.

(Continued)

*Primary Examiner* — Loan H Thanh
*Assistant Examiner* — Shila Jalalzadeh Abyane
(74) *Attorney, Agent, or Firm* — Banner & Witcoff, Ltd.

(57) ABSTRACT

Athletic performance monitoring systems include components for sensing performance data and/or displaying desired information to users. Electronic interface systems facilitate transfer of the data from the performance sensing system to a display device, e.g., to enable the display of athletic performance data on an electronic display device, including conventional electronic display devices that are known and commercially available (e.g., cellular telephones, PDAs, pagers, beepers, MP3 or other audio players, radios, portable televisions, portable DVD players, other video playing devices, watches, etc.). The sensing systems, as well as any data transfer systems associated therewith, may be included as part of an article of footwear, an article of clothing, a piece of athletic equipment, or the like, or even included as part of the interface device.

27 Claims, 8 Drawing Sheets

(56) References Cited

U.S. PATENT DOCUMENTS

| | | | |
|---|---|---|---|
| 2002/0077883 A1 | 6/2002 | Lancos et al. | |
| 2002/0080198 A1 | 6/2002 | Giraldin et al. | |
| 2002/0091796 A1 | 7/2002 | Higginson et al. | |
| 2002/0142887 A1 | 10/2002 | O'Malley | |
| 2002/0147629 A1 | 10/2002 | Alsafadi et al. | |
| 2002/0147642 A1 | 10/2002 | Avallone et al. | |
| 2002/0156677 A1 | 10/2002 | Peters et al. | |
| 2002/0165758 A1 | 11/2002 | Hind et al. | |
| 2002/0173407 A1 | 11/2002 | Bowman | |
| 2002/0174025 A1 | 11/2002 | Hind et al. | |
| 2003/0009308 A1 | 1/2003 | Kirtley | |
| 2003/0009382 A1 | 1/2003 | D'Arbeloff et al. | |
| 2003/0040922 A1 | 2/2003 | Bodin | |
| 2003/0090386 A1 | 5/2003 | Giraldin et al. | |
| 2003/0160732 A1 | 8/2003 | Van Heerden et al. | |
| 2003/0163287 A1* | 8/2003 | Vock et al. | 702/187 |
| 2004/0254650 A1 | 12/2004 | Campagnolo et al. | |
| 2005/0107218 A1 | 5/2005 | Chuang et al. | |
| 2005/0113653 A1* | 5/2005 | Fox et al. | 600/300 |
| 2005/0171410 A1* | 8/2005 | Hjelt et al. | 600/300 |

FOREIGN PATENT DOCUMENTS

| | | | | | |
|---|---|---|---|---|---|
| JP | 2003-154168 A | | 5/2003 | | |
| JP | 2003-175139 | | 6/2003 | | |
| JP | 2003175139 A | * | 6/2003 | | A63B 69/00 |
| JP | 2004-227071 A | | 8/2004 | | |
| JP | 2004-538053 A | | 12/2004 | | |
| WO | 0237732 A2 | | 5/2002 | | |
| WO | 02102240 A2 | | 12/2002 | | |
| WO | 2004-015606 A1 | | 2/2004 | | |
| WO | 2004-038942 A1 | | 5/2004 | | |
| WO | 2004038942 A1 | | 5/2004 | | |

OTHER PUBLICATIONS

Office Action issued in Chinese Application No. 200680030268.3; dated Apr. 10, 2009; English text and translation included.
Chinese Office Action for application No. 200680030268.3 mailed Apr. 14, 2010, 8 pages.
Japanese Office Action for application No. 2008-523963, Sep. 13, 2010.
Japanese Office Action for application No. 2008-523963 dispatched May 25, 2011 and English translation thereof.
The Third Office Action for Chinese patent application No. 200680030268.3 issued Sep. 14, 2011.
European Search Report dated Oct. 7, 2011.
EP Office Action dated Jun. 28, 2012, corresponding Application No. 11/156171.8.
Notice of Reasons for Rejection for Japanese Patent Application No. 2011-207079 mailed Jun. 17, 2013.
Notice of Reasons for Rejection for Japanese Patent Application No. 2008-523963 mailed Sep. 12, 2012.
The First Office Action for Chinese Patent Application No. 201210142690.5 mailed Feb. 25, 2014.

* cited by examiner

INTERFACES AND SYSTEMS FOR DISPLAYING ATHLETIC PERFORMANCE INFORMATION ON ELECTRONIC DEVICES

FIELD OF THE INVENTION

This invention relates generally to athletic performance monitoring systems. Such systems may include components for sensing athletic performance data and/or for displaying desired information to the user. Electronic interface systems in accordance with at least some aspects of this invention facilitate transfer of athletic performance data from the performance sensing system to a processing system and/or a display device, e.g., to enable data input, storage, analysis, and/or display on or by an electronic display device, including on or by conventional electronic display devices that are known and commercially available (e.g., devices that are not typically designed and adapted for displaying athletic performance data).

BACKGROUND

Modern technology has given rise to a wide variety of different electronic and/or communication devices that keep users in touch with one another, entertained, and informed. A wide variety of portable electronic devices are available for these purposes, such as cellular telephones; personal digital assistants ("PDAs"); pagers; beepers; MP3 or other audio players; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries, emergencies, to contact coaches or trainers, etc.), to keep them entertained, to provide information (e.g., time, direction, location, etc.), and the like.

Athletic performance monitoring systems also have benefited from recent advancements in electronic device technology. Electronic performance monitoring devices enable easy and convenient monitoring of many physical or physiological characteristics associated with exercise or other athletic performances, including, for example: speed and distance data, altitude data, GPS data, heart rate, pulse rate, blood pressure data, body temperature, etc. While such data can be collected during an athletic performance, providing this information to a user during the performance and/or enabling user use of and interaction with the data and/or sensors during the performance can be more problematic. For example, requiring the user to carry an additional display device during the athletic performance can be undesirable due to the weight, clumsiness, confusion, and inconvenience of carrying such devices, because users often already have one or more other portable electronic devices that they like to carry (e.g., of the types described above), etc. Moreover, substantial costs may be involved in providing a dedicated athletic performance monitor and/or display device.

SUMMARY

Aspects of this invention relate to athletic performance monitoring systems. Such systems may include components for measuring or sensing athletic performance data and/or for displaying desired information associated with the athletic performance to the user (or others). An electronic interface system or device may be provided to facilitate transfer of the athletic performance data from the sensing system to the display device, e.g., to enable the display of athletic performance data on any electronic display device, including conventional electronic display devices that are known and commercially available (e.g., cellular telephones, PDAs, pagers, beepers, MP3 or other audio players, radios, portable televisions, portable DVD players, other video playing devices, watches, etc.).

Aspects of this invention may include electronic interface devices of the types described above as well as systems and methods in which they are used. Such systems and methods may include: (a) a sensing device for sensing physical and/or physiological data associated with exercise or an athletic performance; (b) a data transfer system in communication with the sensing device for transmitting performance data, wherein the performance data includes at least some portion of the physical or physiological data or data derived, at least in part, from at least some portion of the physical or physiological data; (c) an electronic interface device; and/or (d) a portable display device releasable connected to the interface device, wherein the electronic interface device provides display data to the portable display device, and wherein the display data includes at least some portion of the performance data or data derived, at least in part, from at least some portion of the performance data. The electronic interface device may include, for example: an input system in communication with and adapted to receive the performance data from the data transfer system and an output system having a connection system that includes at least one connection element for physically connecting to the display device. The connection element of the electronic interface device may physically plug into an existing port or jack (such as a universal serial bus port, a parallel port, or other data or power/recharger input port) provided in the display device, including in conventional input ports known and used in commercially available electronic display devices.

If desired, the athletic performance data sensing devices, as well as any data transfer systems associated therewith, may be mounted on (e.g., via a clip, clamp, hook-and-loop fasteners, other fasteners or mechanical structures, adhesives, etc.) and/or included as part of an article of footwear (e.g., integrally formed in or as part of an article of athletic footwear, such as in the sole member), an article of clothing, a piece of athletic equipment, etc. Also, the sensing device and its associated data transfer system, if any, may be included as part of a single overall structure or component, e.g., mounted in a common housing or on a single board, connected or bonded to one another, etc., optionally while sharing a common power source, connectors, and the like, in accordance with at least some examples of this invention.

BRIEF DESCRIPTION OF THE DRAWINGS

A more complete understanding of the present invention and at least some features and advantages thereof may be acquired by referring to the following description and the accompanying drawings, in which like reference numbers indicate like features throughout, and wherein.

DETAILED DESCRIPTION

In the following description of various examples of the present invention, reference is made to the accompanying drawings, which form a part hereof, and in which are shown by way of illustration various structures, embodiments, and examples in which aspects of the invention may be used and practiced. It is to be understood that other embodiments may be utilized and structural and functional modifications may be made without departing from the scope of the present invention.

I. General Description of Aspects of the Invention

Aspects of the present invention relate generally to systems and devices used for athletic performance monitoring, e.g., to measure, process, store, and/or display physical and/or physiological data associated with an athletic event, an exercise routine, or other physical or athletic performance (the term "athletic performance" is used in this specification to generically refer to any type of athletic event, exercise, training, routine, or the like). Some more specific aspects of this invention relate to systems and methods for providing athletic performance data to display devices, to enable display, further processing, and/or storage of the athletic performance information and/or data. In accordance with at least some examples of this invention, the display device may be a conventional and commercially available electronic audio, video, and/or alphanumeric display device (such as a cellular telephone, watch, PDA, pager, MP3 player, audio player, radio, portable television, portable DVD player, video playing device, or the like). At least some examples of the invention may include an "adapter" or other interface system or device: (a) for receiving the data from an athletic performance sensing system and (b) for transmitting data to the display device, optionally with some intervening processing to place the data in a desired form or format, e.g., for immediate display on the display device, storage, etc. The interface system or device may physically plug into an existing port or jack (such as a universal serial bus port, a serial port, a parallel port, or other data or power/recharger input port) provided in the display device, including in conventional input ports known and used in commercially available electronic display devices. This optional feature has advantages in that it provides owners of conventional electronic display devices (e.g., of the types described above) the ability to display, store, and/or retransmit physical or physiological data collected during an athletic performance (e.g., during walking, running, biking, rowing, etc., a user could view performance data (e.g., speed, distance, heart rate, etc.) on a cellular telephone display and/or receive audio information via headphones connected to the cellular telephone or other device with audio capabilities, or the like).

More specific examples of aspects of the invention follow.

A. Electronic Interface Devices

A first aspect of this invention relates to electronic interface devices, e.g., suitable for physical connection to an electronic display device, such as the various conventional and commercially available electronic display devices described above. Such interface devices may include, for example: (a) a housing system; (b) an input system at least partially engaged with the housing system, wherein the input system is adapted to receive input data from one or more external data sources, wherein the input data includes and/or is derived from physical and/or physiological data collected during exercise or an athletic performance; and (c) an output system at least partially engaged with the housing system, wherein the output system includes a connection system that includes at least one connection element for physically and releasably engaging an input port of a portable external electronic device, wherein the output system is adapted to provide output data to the portable external electronic device, and wherein the output data includes at least some portion of the input data or data derived, at least in part, from at least some portion of the input data.

Various other elements or components may be included with electronic interface devices, if desired, in accordance with at least some examples of this invention. For example, electronic interface devices according to at least some examples of the invention further may include a processing system, optionally at least partially located within or engaged with the housing system, for receiving the input data and/or for supplying the output data to the output system (optionally after converting the data into another form or other data processing). Electronic interface devices in accordance with at least some examples of this invention further may include a memory system, optionally at least partially located in or engaged with the housing system, for storing at least some portion of the input data or data derived, at least in part, from at least some portion of the input data. If desired, data may be stored in the electronic interface device and made available for later analysis (e.g., for post exercise analysis), optionally after download or transmission to a computer or other processing system. As still another example, if desired, electronic interface devices according to at least some examples of this invention further may include a separate power supply, at least partially within or engaged with the housing system, for providing power to at least one of the output system or the input system (e.g., a rechargeable battery system, a battery power supply, and/or an AC/DC power supply input).

B. Athletic Performance Monitoring Systems Including a Performance Sensor and an Electronic Interface Device Another aspect of this invention relates to athletic performance monitoring systems that include a sensor for sensing athletic performance data and an electronic interface device, e.g., of the types generally described above. Such athletic performance monitoring systems may include, for example: (a) a sensing device for sensing physical or physiological data associated with an athletic performance; (b) a data transfer system in communication with the sensing device for transmitting performance data, wherein the performance data includes at least some portion of the physical or physiological data or data derived, at least in part, from at least some portion of the physical or physiological data; and (c) an electronic interface device. The electronic interface device of this example system may include, for example: an input system in communication with the data transfer system for receiving the performance data; and an output system having a connection system that includes at least one connection element for physically and releasably engaging an input port of a portable electronic display device, wherein the output system is adapted to provide display data to the portable electronic display device, and wherein the display data includes at least some portion of the performance data or data derived, at least in part, from the performance data.

Other athletic performance monitoring systems according to at least some examples of the invention include a sensing device within and/or as part of the same component as the electronic interface device. Such athletic performance monitoring systems may include, for example: (a) a housing system; (b) a sensing device at least partially included in or on or otherwise engaged with the housing system for sensing physical or physiological data associated with an athletic performance; (c) a data transfer system in communication with the sensing device for transmitting performance data, wherein the performance data includes at least some portion of the physical or physiological data or data derived, at least in part, from at least some portion of the physical or physiological data; and (d) an output system at least partially engaged with the housing system, wherein the output system includes a connection system that includes at least one connection element for physically and releasably engaging an input port of a portable electronic display device, wherein the output system is adapted to provide display data to the portable electronic display device, and wherein the display data includes at least some portion of the performance data or data derived, at least in part, from the performance data.

Any type of athletic performance data may be sensed and transferred to the electronic interface device, optionally in any form or format, without departing from this invention. As more specific examples, athletic performance monitoring systems in accordance with at least some examples of this invention may sense and/or transmit: user speed data; user distance data; GPS data; altitude data; route data; user step count data; contact surface impact force data; ambient temperature data; ambient humidity data; barometric pressure data; sole member compression data; jump height data; pulse rate data; heart rate data; blood pressure data; body temperature data; air intake rate or volume data; air expel rate or volume data; EKG data; EEG data; blood gas data; and the like. Additionally, if desired, multiple different types of data may be sensed and/or transmitted to the electronic interface device including, for example, combinations of the various different types of data described above. Optionally, the electronic interface device may receive performance data from multiple data sensors or sources, optionally with some sources independent of the electronic interface device and/or other sources included with or as part of the electronic interface device.

C. Athletic Performance Monitoring Systems Including an Electronic Interface Device and a Display Device Another aspect of this invention relates to athletic performance monitoring systems that include electronic interface devices, e.g., of the types generally described above, in combination with (e.g., physically connected to) electronic display devices. Such systems may include, for example: (a) an electronic interface device including: (i) an input system adapted to receive performance data from one or more external data sources, wherein the performance data includes or is derived from physical or physiological data collected during an athletic performance; and (ii) an output system that includes a connection system having at least one physical connection element; and (b) a portable display device releasable connected to the connection element, wherein the output system provides display data to the portable display device via the connection system, and wherein the display data includes at least some portion of the performance data or data derived, at least in part, from at least some portion of the performance data. The performance data or data derived at least in part from the performance data may be displayed on the display device, if desired, in real time as the athletic performance continues and/or stored (in the interface device or the display device) for later download, use, processing, and/or analysis.

If desired, in accordance with at least some examples of this invention, the processing system of the display device may be used to control operations of the electronic interface device or even the performance data sensing systems, such as the data transfer system (from the sensor to the interface device), the data receiving system, data transfer to the display device for display, data storage (e.g., in memory on board the display device and/or the electronic interface device), interfacing with the user, data demands or requests, etc. The display device may include software, e.g., downloaded thereto, to enable control of the various features and/or functions of the electronic interface device (alternatively, if desired, the software and/or control functions may be driven by processing capabilities possessed by the electronic interface device, such as a processing system provided with the interface device). As a more specific example, if desired, the software may constitute a Java application that ships with the display device or the interface device and/or is downloaded thereto at a later time. As additional examples, a user may purchase an interface device of the types described above and obtain software (e.g., as a disk purchased with the interface device, downloaded from a remote or external source, etc.) to format the interface device to properly interact with one or more electronic devices used by the user (e.g., the software may be designed to enable the interface device to format its output to match the requirements of the specific cell phone, PDA, MP3 player, etc. models used by the user). Also, if desired, commands sent from the display device to the electronic interface device may be used, for example, to power the interface device on and off, to set up radio transceiver parameters and controls, to set up other functions or controls (such as display preferences, data collection preferences, data update, refresh, or report rates, etc.), and the like. The display device may be capable of receiving data from the electronic interface device synchronously or asynchronously.

As noted above, aspects of this invention may be practiced with any type of display device without departing from the invention including, for example, conventional display devices known and commercially available (also called "off the shelf" audio or video communication or display devices herein). More specific examples of suitable display devices include: electronic devices with a display screen, such as an LED, LCD, or plasma display screen; watches; portable audio devices, such as radios, tape players, CD players, MP3 players, and the like; alphanumeric display devices such as beepers, pagers, and the like; portable video or audio/video display devices, such as televisions, DVD players, and the like; portable communication devices, such as cellular telephones, radios, and the like; portable computing systems, such as personal digital assistants, handtop or palm top computing systems, and the like.

D. Athletic Performance Monitoring Systems Including a Sensing Device, an Electronic Interface Device, and a Display Device Still another aspect of this invention relates to systems for athletic performance monitoring that include components both for sensing the athletic performance data and for displaying desired information to the user (or others). Such systems may include: (a) a sensing device for sensing physical or physiological data associated with an athletic performance; (b) a data transfer system in communication with the sensing device for transmitting performance data, wherein the performance data includes at least some portion of the physical or physiological data or data derived, at least in part, from at least some portion of the physical or physiological data; (c) an electronic interface device; and (d) a portable display device physically and releasably connected to the interface device, wherein the electronic interface device provides display data to the portable display device, and wherein the display data includes at least some portion of the performance data or data derived, at least in part, from at least some portion of the performance data. The electronic interface device further may include: an input system in communication with and adapted to receive the performance data from the data transfer system and an output system having a connection system that includes at least one physical connection element for connecting to the display device.

E. Other Features and Aspects of the Invention

Many other features and characteristics may be provided in accordance with the various example aspects of the invention described above. For example, the connection system included as part of the electronic interface device may take on various forms and/or shapes without departing from the invention. As more specific examples, the connection system may include a plug or other element designed so as to be received in or engaged with a conventional data or power input port of conventional electronic devices, e.g., of the types described above. Such input ports may include serial ports, parallel ports, universal serial bus ports, power supply/battery recharging ports, data input ports, and the like. If desired, the connection system also may include one or more power supply connectors so that the power source (e.g., the battery, etc.) from the portable display device also may be relied upon to operate the various devices in the electronic interface device. In such systems, the electronic interface device need not include its own independent power supply, thereby enabling reductions in the size, weight, and expense of the electronic interface devices.

Any type of input system to the electronic interface device also may be provided without departing from this invention. As more specific examples, the input system may include a wireless data receiving system for receiving input data from at least one external data source (e.g., from the sensing device(s) that sense the athletic performance data, from a computer or network, etc.), a wire or other physical connection system (optionally with one or more connection elements provided on the sensing device for plugging the external data source into the interface device), etc. Interface device formatting data (e.g., for formatting the output for delivery to specific electronic display devices, etc.) and other data, if any, may be received by the interface device via the same input system that allows it to receive the physical or physiological data, or through another input system, if desired. The electronic interface device additionally or alternatively may include a user input system, optionally at least partially in or on a housing system for the interface device. User input may be received at the interface device for any desired purpose, such as for inputting requests for certain display information, requests for certain sensed information, display or sensor control information, requests for data or information from other sources, etc., and for providing formatting information (e.g., identifying target electronic display devices to enable providing output data in formats that will work with the specific display device(s), etc.) or other information, etc. Examples of the user input systems may include buttons (hard or soft), voice command input systems, stylus input command systems, touch screen input command systems, slide or switch systems, and the like.

The sensing systems for sensing the athletic performance data (e.g., the detected physical or physiological data associated with the athletic performance) may be provided in any desired form or structure and/or for measuring any desired data or parameter without departing from this invention. As more specific examples, if desired, the sensing system and/or devices, as well as any data transfer systems associated therewith, may be mounted on (e.g., via a clip, clamp, hook-and-loop fasteners, or other fasteners or mechanical structures, adhesives, etc.) and/or included as part of an article of footwear (e.g., integrally formed in or as part of an article of athletic footwear), an article of clothing or apparel, a piece of athletic equipment, etc. If desired, the sensing devices and any associated data transfer systems may be included as part of a single structure, e.g., mounted in a common housing, connected to one another, etc.

II. Specific Examples of the Invention

While aspects of the invention generally have been described above, the following detailed description, in conjunction with FIGS. 1-9, provides even more detailed examples of electronic interface devices and athletic performance monitoring systems and methods in accordance with examples of this invention. Those skilled in the art should understand, of course, that the following description constitutes descriptions of examples of the invention and should not be construed as limiting the invention in any way.

Figure 1:
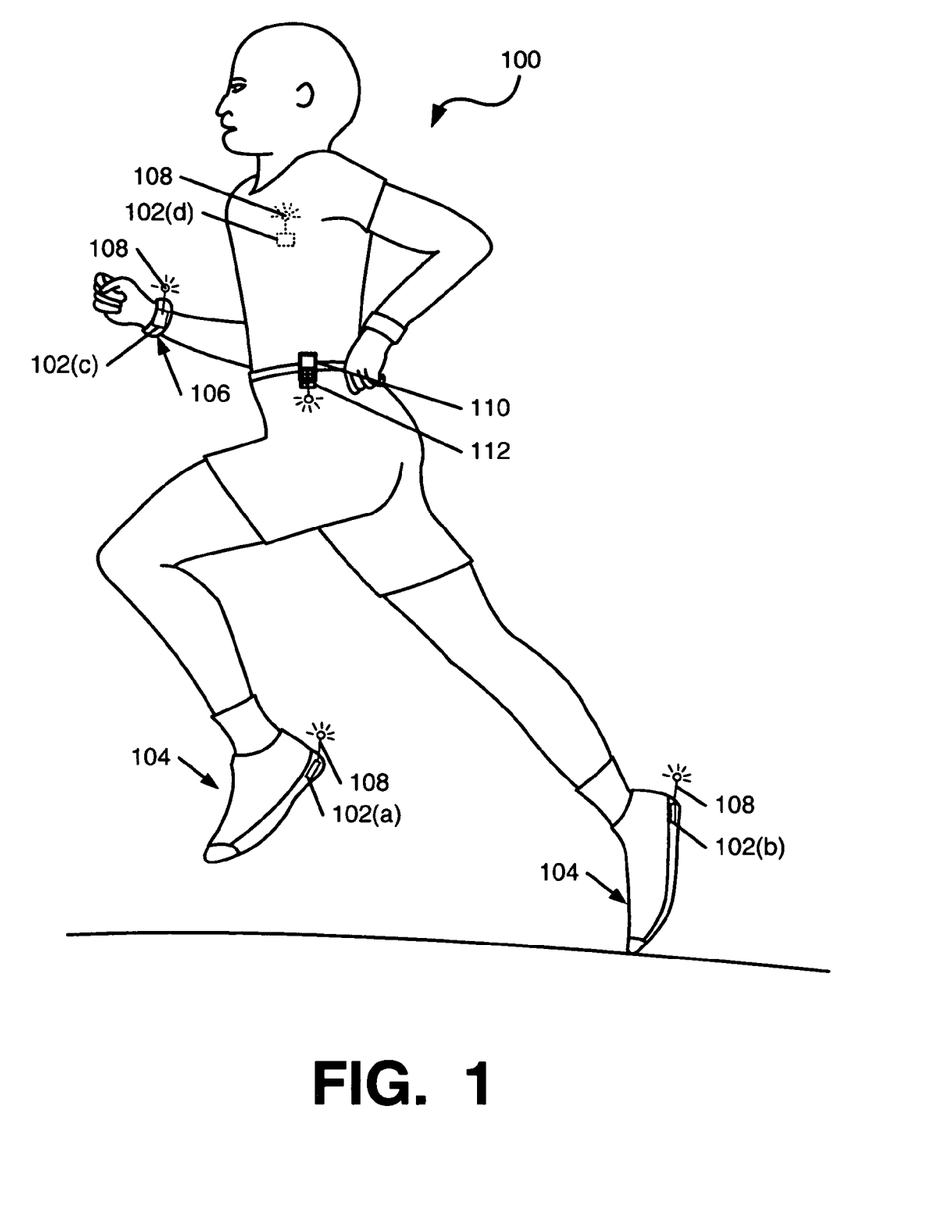
FIG. 1 illustrates example systems and an example environment in which various aspects and features of the invention may be used.

FIG. 1 illustrates example systems and an environment in which various aspects of the present invention may be used. As shown in FIG. 1, a person 100 involved in an athletic performance may have one or more sensing devices 102(a), 102(b), 102(c), and 102(d) included on their person, their clothing, their footwear, or their equipment. These sensing devices may sense data associated with the athletic performance, including, for example, physical or physiological data associated with the athletic performance. As some more specific examples, in the environment illustrated in FIG. 1, sensors 102(a) and/or 102(b) may sense step count (e.g., for pedometer type speed and/or distance measuring), GPS data, step impact force data (e.g., for active impact attenuation control), jump height data, or the like; sensor 102(c) may sense pulse rate, body temperature, blood pressure, hydration levels, or the like; and sensor 102(d) may sense heart rate, EKG data, and the like. Of course, any number of sensors may be provided and such sensors may sense any desired type of athletic performance information without departing from this invention. Additional examples of potential types of data relating to an athletic performance that may be collected include, but are not limited to: user speed data; user distance data; GPS data (e.g., location data); altitude data; route data; user step count data; contact surface impact force data; ambient temperature data; ambient humidity data; barometric pressure data; sole member compression data; jump height data; pulse rate data; heart rate data; blood pressure data; body temperature data; hydration level data; air intake rate or volume data; air expel rate or volume data; EKG data; EEG data; blood gas content data; and the like.

The various sensors, e.g., 102(a) through 102(d), also may be portable and carried by the person 100 in any desired manner without departing from this invention. For example, if desired, one or more sensors may be mounted in or on an article of footwear 104 (e.g., like sensors 102(a) and 102(b) in this example), provided in or on an article of athletic apparel (e.g., like arm band 106 in this example, which includes sensor 102(c), in a shirt, shorts, pants, socks, headband, etc.), and/or carried along on a piece of athletic equipment (e.g., like a bicycle, bat, racket, club, vehicle, ball, etc.). As still additional examples, as illustrated in FIG. 1, a sensing device 102(d) may be mounted directly on the athlete's 100 body, e.g., by adhesives, bands, hooks, other mechanical connectors, or the like.

The sensing systems and/or devices 102(a) through 102(d), as well as any data transfer systems associated therewith (e.g., such as wireless transmission or transceiver devices 108 shown in FIG. 1 and described more below (e.g., radio transceivers)), may be mounted on articles of footwear, clothing, athletic equipment, or the like in any desired manner, e.g., via clips, clamps, adhesives, sewing, in pockets, via hook-and-loop fasteners, or other fasteners or mechanical structures, etc. Alternatively, if desired, the sensing systems or devices 102(a) through 102(d) may be integrally formed with and/or included as part of an article of footwear, an article of clothing, a piece of athletic equipment, etc. without departing from the invention (e.g., mounted therein, optionally in a permanent or freely removable manner, etc.) If desired, one or more sensing devices and its/their associated data transfer system(s) 108 may be included as part of a single structure, e.g., mounted in a common housing and/or on a common board, connected to one another, etc., without departing from this invention. Further, if desired, the housing (if any) may be equipped with operation lights (e.g., LEDs, etc.) or other indicators, e.g., to indicate power status (e.g., on/off), power source status (e.g., charging v. battery operation), data reception and/or processing status (e.g., standby v. receiving v. transmitting v. processing, etc.), charge or recharging level status, etc.

In accordance with at least some example aspects of this invention, physical or physiological data associated with an athletic performance may be collected by the various sensing devices (e.g., devices 102(a) through 102(d)) and transmitted to a display device 110 for display (and optionally storage, further processing, etc.). Any type of display device 110 may be used without departing from the invention, including, for example, conventional or "off the shelf" display devices 110. More specific examples of suitable display devices 110 include: electronic devices with a display screen, such as an LED, LCD, or plasma display screen; watches; portable audio devices, such as radios, tape players, CD players, MP3 players, and the like; alphanumeric display devices such as beepers, pagers, and the like; portable video or audio/video display devices, such as portable televisions, DVD players, and the like; portable communication devices, such as cellular telephones, radios, and the like; portable computing systems, such as PDAs, handtop or palm top computing systems, and the like. In the illustrated example, the display device 110 includes a cellular telephone that the user has clipped to his belt so as to be readily carried and used during the athletic performance. The use of this type of arrangement is advantageous in at least some situations because the athletic performance data may be displayed on the display system of the cellular telephone 110, and thus the user need not carry another entire display device to enable display of the athletic performance data (thereby reducing weight and expense).

One cannot just simply begin transmitting athletic performance data from sensing devices 102(a) through 102(d) to a conventional cellular telephone 110 and expect the telephone 110 to operate to receive this data and display it in the desired format (and/or in a user controllable form or format). Accordingly, as illustrated in FIG. 1 and in more detail in FIG. 2, systems and methods in accordance with at least some examples of this invention may include an electronic interface device 112 that physically plugs into the display device 110 (e.g., in a releasable manner) and is carried along with the display device 110 during the athletic performance. As shown in more detail in FIG. 2, the electronic interface device 112 of this example includes a connector system 114 that physically plugs into and connects with conventional input ports 116 provided on this display device 110 model. The input port 116 into which the connector system 114 of the interface device 112 connects may be any type of input port provided on a display device 110, such as data input ports (e.g., parallel ports, serial ports, USB ports, earphone or other jacks or ports, etc.), e.g., like input ports used in conventional electronic devices for data input, recharging, AC power supply, etc. The connector system 114 may include suitable connecting devices, such as wires, pins, electrical connectors, and the like, so as to make electrical connection or other suitable connections with corresponding elements provided in the input port 116 of the display device 110 (e.g., to allow electronic and/or data communications between the interface device 112 and display device 110). If necessary or desired, additional securing elements may be provided to securely hold the interface device 112 together with the display device 110, such as straps, hooks, buckles, clips, clamps, clasps, retaining elements, mechanical connectors, and the like.

Figure 2:
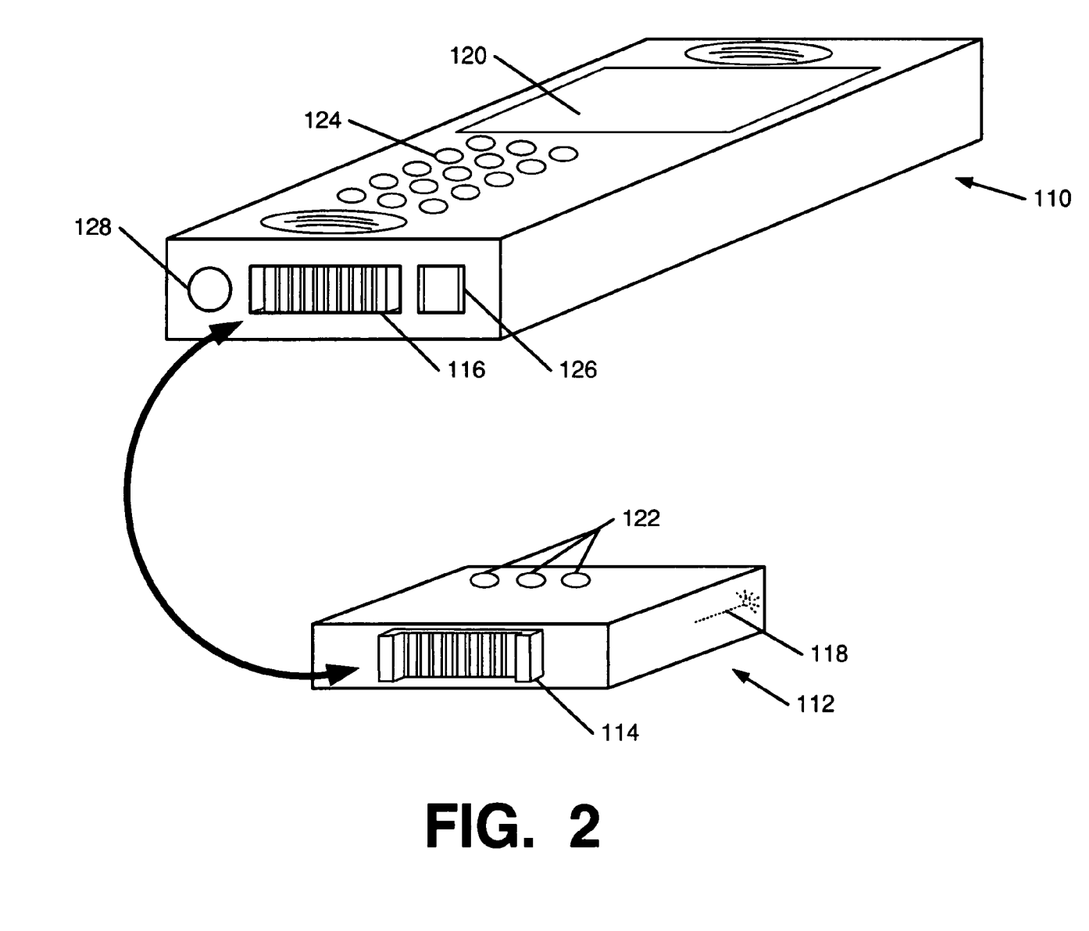
FIG. 2 illustrates an example electronic interface/display device combination in accordance with at least some examples of this invention.

In operation, the electronic interface device 112 may receive signals from one or more external sources, such as the various sensing devices 102(a) through 102(d), e.g., transmitted via data transfer systems 108 included with the sensing devices 102(a) through 102(d) to a data receiving device or system 118 provided in or with the interface device 112 (e.g., a wireless receiver of transceiver device, a radio transceiver, infrared receiver, light source receiver, etc.). If desired, data transfer system 108 and data receiving system 118 each may include the capability of receiving input data and transmitting output data without departing from this invention (of course, separate reception and transmission devices or systems may be provided on each of the sensing devices 102(a) through 102(d) and interface device 112, if desired). While a wireless communication protocol is illustrated in FIGS. 1 and 2, of course, any desired manner of communicating between the sensing devices 102(a) through 102(d) and the interface device 112 may be used without departing from the invention, including wired connections, if desired. Signals from the sensors 102(a) through 102(d), optionally after data processing in the interface device 112 to place them in a form or format for display and/or use by the display device 110, are transferred from the interface device 112 to the display device 110 via connector system 114 (which is physically plugged into input port 116 of the display device 110). Once input to the display device 110, the input data may be further processed if necessary or desired and then displayed to the user in desired form on the display panel 120.

Of course, any desired way of placing data derived from the physical or physiological data from the sensing devices 102(a) through 102(d) in the proper form or format for display on display device 110 may be provided without departing from the invention. As examples, if desired, the interface device 112 may be specially designed and/or programmed for use with one or more specific electronic devices 110 (e.g., preprogrammed to operate with a specific device or devices and to provide output data in a form and format suitable for those devices). In this situation, the interface devices 112 may be marketed and sold specifically targeted to certain electronic display devices 110. As another alternative, if desired, the interface devices 112 may be programmed at a later time to operate with a wide variety of different electronic devices 110, e.g., by downloading display driver and/or format data for specific display devices 110 from the internet, from disk or another source; etc. As a more specific example, when the user plugs the interface device 112 into an electronic device 110 (e.g., for the first time), signals exchanged between the interface device 112 and the electronic device 110 may identify the devices to one another and/or otherwise enable the processing system of one of the devices to download driver or set up information from a remote or external source, such as the internet, from a disk, from memory included with the interface device 112, etc., akin to the manner in which personal computer devices recognize newly attached hardware (e.g., a mouse, printer, scanner, etc.) and/or perform various setup operations associated with newly added hardware or software. Of course, other ways of assuring that the data is placed in proper form or format for display may be used without departing from this invention. The processing to place the data in the form and/or format for display may take place in the interface device 112, in the display device 110, and/or at any other desired component without departing from this invention.

If desired, in accordance with at least some examples of this invention, the electronic interface device 112 further may include a user input system, such as one or more buttons 122 provided in the illustrated example shown in FIG. 2. This user input system 122 may be used, for example: to control one or more aspects of the processing of the input data received via data receiving device 118, to control input data receipt (e.g., timing, types of information received, on-demand data requests, etc.), to control data output to the display device 110, to control the sensing devices 102(*a*) through 102(*d*), etc. Alternatively or additionally, if desired, the input system on the display device 110 (e.g., buttons 124, a touch screen, a digitizer/stylus based input, etc.), may be used to provide user input data to the interface device 112 and/or to the sensing devices 102(*a*) through 102(*d*) or the sensing systems (e.g., if the connector system 114 or other portion of the interface device 112 is designed to accept input from the display device 110). As still another example, if desired, a voice input system may be provided with the interface device 112 and/or the display device 110, e.g., to enable user input via voice commands. Any other desired type of user input system, for control of any system elements and/or for any purpose, may be provided without departing from the invention.

The display device 110 may include additional input elements, e.g., such as ports 126 and 128 shown in FIG. 2 for headphones, power supplies, wireless communications, infrared input, or other devices. If desired, and if these ports 126 and 128 are covered when the interface device 112 is attached to the display device 110, the interface device 112 may be equipped with similar external ports to ports 126 and 128, and internal circuitry may be provided in the interface device 112 to enable the user to plug the same additional devices into the interface device 112 as they might plug into the display device 110 and still take advantage of the same functions (e.g., to thereby allow the necessary data, signals, and/or information to pass through the interface device 112 to the user and/or to the display device 110).

Figure 3:
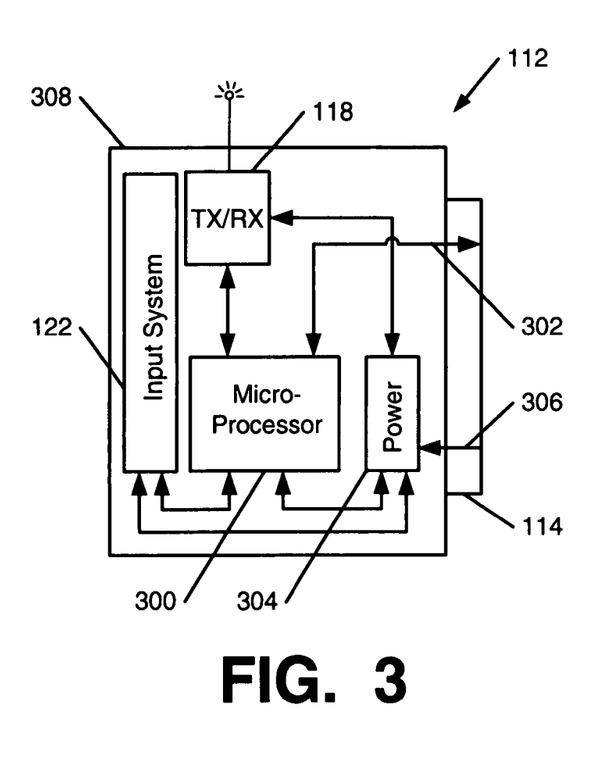
FIG. 3 illustrates a schematic diagram showing components provided in one example of an electronic interface device in accordance with this invention.

FIG. 3 includes a schematic diagram of various example components that may be included in an electronic interface device 112 in accordance with at least some examples of this invention. As shown in FIG. 3 and described above in conjunction with FIGS. 1 and 2, the interface device 112 may include a connection system 114 for physically connecting to a display device, and a data reception system 118 (e.g., a wireless data receiver or transceiver, an infrared receiver, etc.) for receiving input data from an external source, such as a sensor for sensing athletic performance data, a computer, network, or other processing system, etc. Additionally, as further shown in FIG. 3, the interface device 112 may include an input system 122 for receiving user input, e.g., via keys, touch screen, digitizer, voice input, stylus input, etc.

In accordance with at least some examples of this invention, the electronic interface device 112 further may include a processing system, e.g., microprocessor 300, for performing various operations, e.g., for operating the electronic interface, interacting with the external data source(s), receiving user input from one or more sources (e.g., via input system 122, via computer or network connections, etc.), and/or for interacting with the display device (e.g., via output supplied to the display device through wire or pin connections 302 included with the connection system 114. Of course, any number of wire, pin, or other connections may be provided via connection system 114 to provide suitable electronic/data communications between the interface device 112 and an external display device (e.g., like the connection systems provided on cellular telephones, PDAs, or other portable electronic devices, including conventional electronic devices known and commercially available). The connector system 114 may be designed to match the display device into which it plugs so as to provide a path for electronic/data communications between the interface device 112 and the display device (e.g., device 110). Moreover, if desired, microprocessor 300 may include operating system software and/or may process the input data from the sensing device, in accordance with at least some examples of this invention, to transform the data into suitable forms for receipt by, use in, and/or display by the display device, to change the data form or format, to make calculations based on the raw input data, etc.

FIG. 3 further illustrates a power supply device 304 included as part of the electronic interface device 112. This power supply device 304 may include a conventional battery, e.g., a rechargeable battery, as is commonly known and used in the electronics art. Alternatively or additionally, if desired, the power supply device 304 may receive power input from the display device to which it is attached (e.g., through input pin, wire, or line 306 or other connection system) and use the power source from the display device to operate the various elements and components in the interface device 112, (e.g., the microprocessor 300, the data receiving system 118, the input system 122, any operating lights or displays, and the like). As still another example, if desired, the power supply 304 may connect to an external power source, such as an AC power supply, a battery power source, etc.

If desired, some or all of the various parts illustrated in FIG. 3 may be mounted, housed, or contained in or on a housing system 308 or otherwise formed as a convenient module or package. The connection system 114 may at least partially extend out of the housing 308, may be integrally formed as part of the housing 308, may be a separate element fixed to the housing 308 (e.g., by adhesives or connectors, etc.), or otherwise may be available and/or included with the housing system 308.

Figure 4:
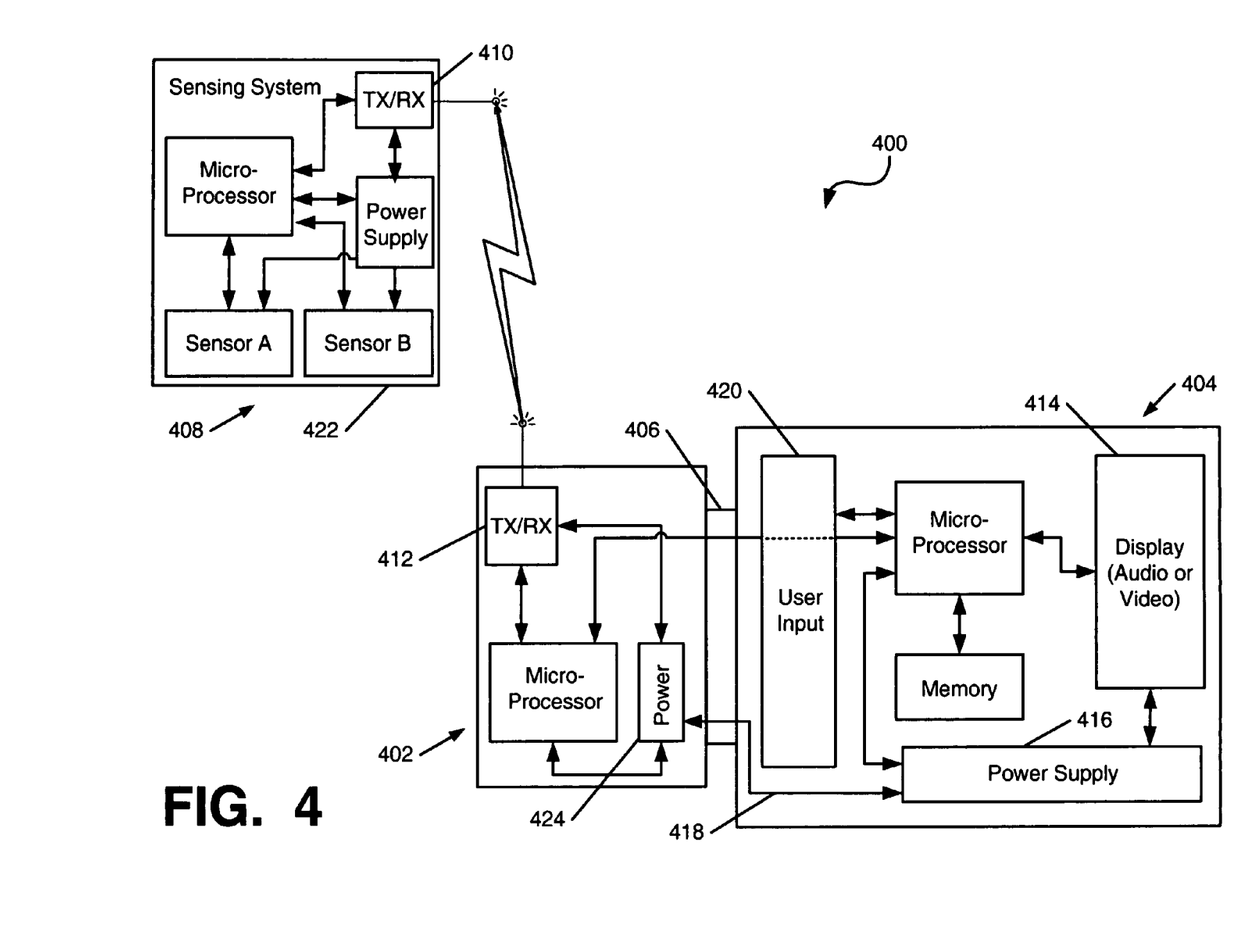
FIG. 4 illustrates a schematic diagram showing components provided in one example of an athletic performance monitoring system in accordance with this invention.

FIG. 4 illustrates a schematic diagram of an overall athletic performance monitoring system 400 in accordance with at least some examples of this invention. In this system 400, an electronic interface device 402 is physically plugged into a portable electronic display device 404 via a mechanical connection system 406 that holds the two devices together, e.g., in a secure but releasable manner (e.g., via friction fit, detents or retaining elements, etc.). Optionally, if desired, other independent securing elements may be provided to at least partially help hold the interface device 402 with the portable electronic display device 404 (e.g., hooks, straps, snaps, clips, clamps, clasps, retaining elements, etc.).

This example system 400 further includes a sensing system 408 for measuring and transmitting athletic performance data. More specifically, in this example structure, athletic performance data (e.g., physical or physiological data associated with the athletic performance) is sensed by sensors A and B, and data from these sensors is sent to the sensing system's processing system, e.g., a microprocessor, which optionally may cause the data to be stored (e.g., in a storage system or memory (not shown in FIG. 4), further processed, etc. A separate power supply may be provided to operate the various components of the sensing system 408, such as the sensors, the microprocessor, the data transfer system 410, memory, and/or any other necessary or desired components. If desired, the microprocessor on board the sensing system 408, if any, may process the sensor data, change its form or format, or otherwise manipulate the data prior to sending it on to other parts of the system 400.

At an appropriate or desired time (e.g., when a data request is received, periodically, automatically, upon user demand, etc.), the sensing system 408 may send at least some portion of its data (e.g., raw data directly from one or more of the sensors, data derived at least in part from the raw data, etc.) to the electronic interface device 402, e.g., for eventual display to a user on display device 404. This may be accomplished, for example, as shown in FIG. 4, via a wireless data transmission system (e.g., from wireless data transfer or transmission element 410 in the sensing system 408 to wireless data receiving element 412 in the electronic interface device 402) or in any other desired manner without departing from this invention. Any desired wireless protocol, broadcast protocol, or other data transmission protocol may be used without departing from this invention.

Once received at the electronic interface device 402, the athletic performance data may be further processed, if necessary or desired, and then supplied to the processing system (e.g., microprocessor) of the display device 404. This may be accomplished at any desired time or timing (e.g., when a data request is received, automatically, periodically, on user demand, etc.) without departing from this invention. From there, the data may be further processed, if necessary or desired, and then sent to the display screen 414 in a form suitable for presentation to and viewing by a user (e.g., in audio, video, and/or alphanumeric form, etc.).

In this illustrated example system 400, power for the electronic interface device 402 is supplied via the power supply 416 used for operating the display device 404 (e.g., which may be a rechargeable battery of a cellular telephone or other portable electronic device), as shown by the connection 418 to the power supply 416 via the connection system 406. The "power" element 424 in interface device 402 in this example may be used simply to distribute power from an external power source (e.g., the power supply 416 of display device 404 in this example) to various components of the interface device 402. Alternatively, the power element 424 may be omitted, e.g., if internal wiring of the interface device 402 allows power transfer from power supply 416 to all required components of the interface device 402. Additionally, in this example system 400, user input may be furnished to control the electronic interface device 402 via input systems 420 provided in the portable display device 404. For example, if desired, a user could enter a specific mode of operation via inputs provided on the display device 404 in which various features, functions, or characteristics of the electronic interface device 402 may be controlled. Additionally or alternatively, if desired, the electronic interface device 402 may include its own input system and/or its own power supply, e.g., as described above in conjunction with FIG. 3, without departing from this invention (however, utilizing these components and resources from the display device 404 helps reduce the overall size, weight, and cost of the interface device 402).

Of course, many different arrangements of various elements or components, including some or all of the elements or components shown in FIG. 4, may be used without departing from this invention. Moreover, additional components or elements may be included in such systems, or one or more of the illustrated systems or components may be eliminated without departing from the invention. Additionally, if desired, a single electronic interface device 402 and display device 404 may be simultaneously operatively connected so as to receive data input from multiple independent sensing systems, e.g., of the type shown at reference number 408 (see, for example, the arrangement of FIG. 1). Many variations in the overall structures, components, and architectures of various systems are possible without departing from this invention.

One potential advantage of systems and methods according to at least some examples of this invention lies in the fact that the components and infrastructure of an existing portable electronic display device (e.g., a cellular telephone, MP3 player, PDA, or the like) may be leveraged and used in combination with an electronic interface device that connects thereto and electronically communicates therewith in order to allow this existing electronic device to additionally display and provide athletic performance data to a user without requiring the user to obtain and carry another electronic display device. As noted above, leveraging the input system and/or power supply of the existing electronic device used for its display can further reduce the size, weight, cost, and complexity of the interface device, thereby providing additional advantages.

Figure 5:
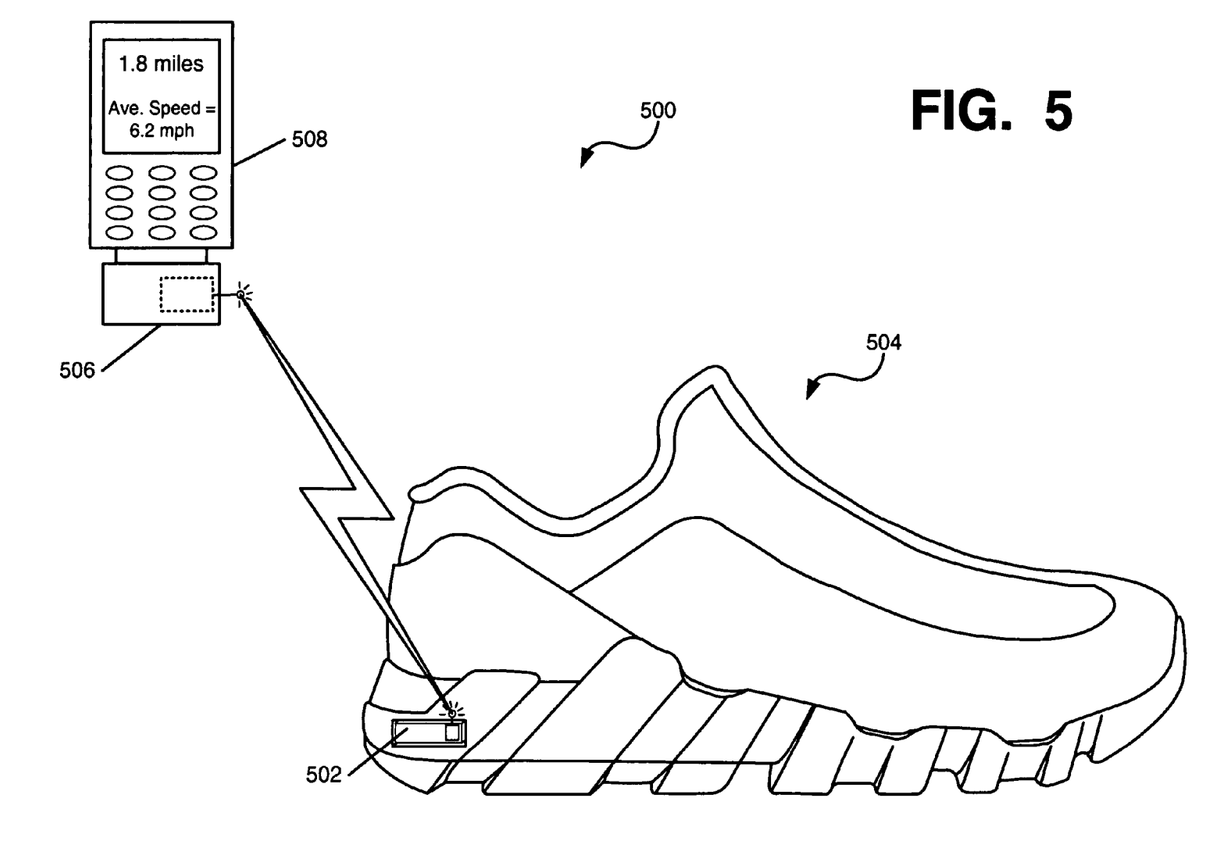
FIG. 5 illustrates an example of an athletic performance monitoring system in accordance with this invention in which the athletic performance data sensor or collection device is mounted in an article of footwear.

The athletic performance sensing systems may be provided in a wide variety of different environments without departing from the invention. For example, as illustrated in FIG. 4, if desired, one or more sensors for sensing data associated with an athletic performance (e.g., physical or physiological data) may be provided in a housing 422, optionally along with at least a portion of a data transfer system (e.g., wireless transmission or transceiver device 410) and/or other processing or electronic components, e.g., to provide an athletic performance data sensing module or system 408. When provided as a module or otherwise provided as separate elements, these portions of athletic performance sensing systems (e.g., 408) may be provided at any desired location without departing from the invention, e.g., assuming their data sensing, processing, and/or transmitting capabilities are not compromised by the positioning. FIG. 5 illustrates an example system 500 in which an athletic performance sensing module 502 is mounted in an article of athletic footwear 504. The sensing module 502 may include, for example, one or more athletic performance data sensors, a data transfer system, processing capabilities, a power supply, and/or the like (e.g., like the system 408 shown in FIG. 4). Any desired manner of mounting the sensing module 502 in or on the article of footwear 504 may be provided without departing from the invention, such as via a slot or chamber, via a mounting pocket or element, via straps, adhesives, mechanical connectors, hookand-loop fasteners, retaining elements, via user removable connections, etc. Alternatively, if desired, the sensing module 502 may be integrally formed as part of the article of footwear 504, e.g., during footwear manufacture, and/or permanently fixed thereto.

As further shown in FIG. 5, the sensing module 502 may be in wireless (or other) communication with an interface device 506, which in turn is physically connected to a display device 508, such as a cellular telephone as illustrated in FIG. 5. This display device 508 may be attached to the user's body, clothing, or equipment, e.g., so as to be easily carried, moved, and/or viewed during the athletic performance. In general, any of the various athletic data performance sensing systems, electronic interface devices, and/or portable electronic display devices of the types described above in conjunction with FIGS. 1-4 may be used without departing from this invention. As more specific examples, if desired, the sensing devices aboard sensing module 502 may provide step count data, and the electronic interface device 506 may process this data, optionally along with timing data, so as to provide pedometer type speed and/or distance data for display on display device 508. Of course, any type of data may be provided by sensing modules 502 and any desired type of information may be displayed on display device 508 without departing from this invention.

Figure 6:
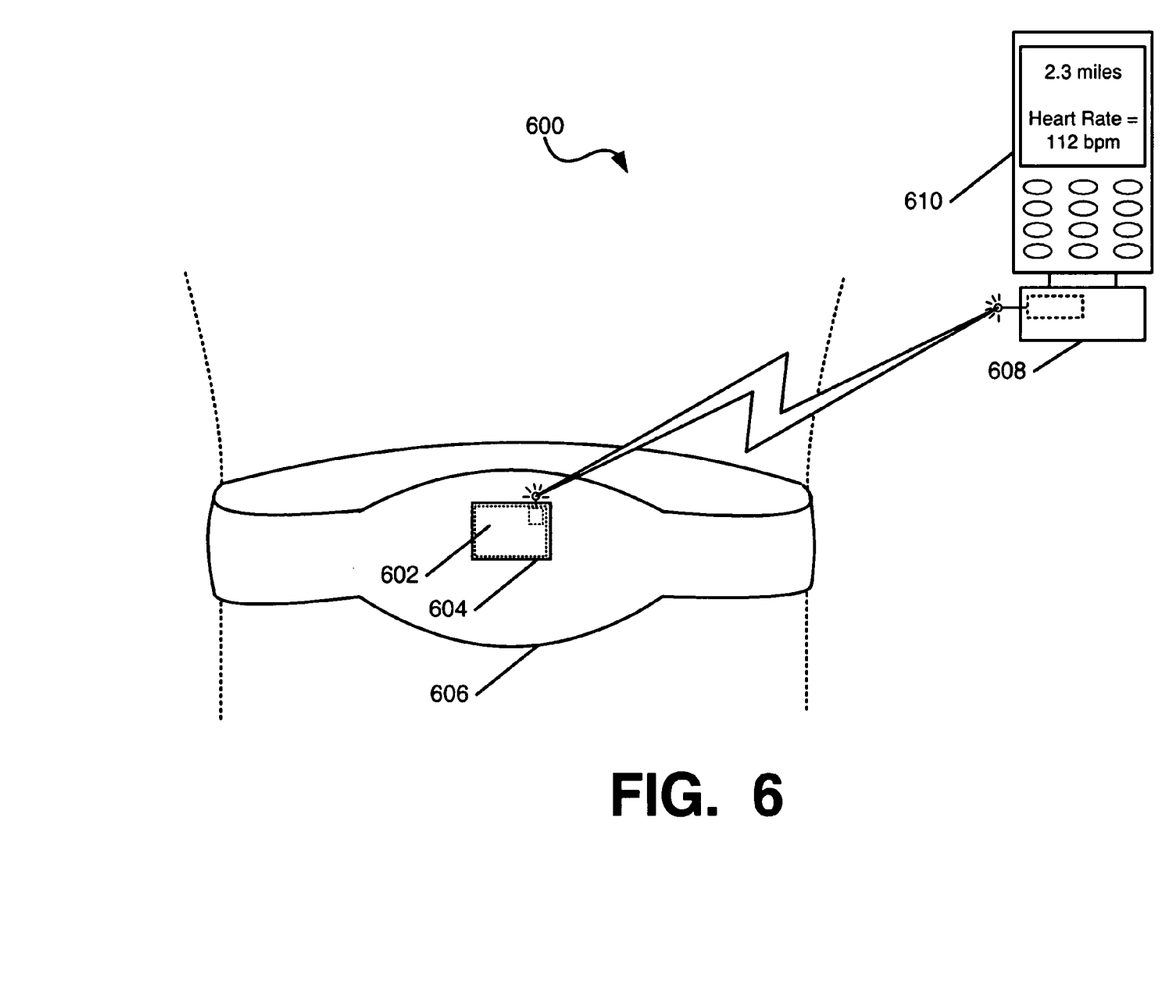
FIG. 6 illustrates an example of an athletic performance monitoring system in accordance with this invention in which the athletic performance data sensor or collection device is mounted in an article of apparel.

FIG. 6 illustrates another arrangement and/or environment of use of systems 600 according to at least some examples of this invention. In this example, the sensing device 602, including one or more individual sensing elements for measuring athletic performance data, is mounted in or on an article of clothing, such as in a pocket or other attachment element 604 provided in a belt or band 606. The belt or band 606 or other article of apparel may be attached to the user's body (e.g., arm, waist, chest, leg, head, etc.) and may be arranged so that the sensing elements on board sensing device 602 measure the desired data (e.g., physical data associated with the athletic performance, such as step count, speed, distances, impact force, etc., or physiological data, such as heart rate, pulse rate, air intake/exhale volumes or rates, body temperature, blood pressure, EKG data, EEG data, etc.). The measured data may be transmitted to the electronic interface device 608, optionally after initial processing, which in turn may further process the incoming data and transfer it on to display device 610 for display to the user.

Figure 7:
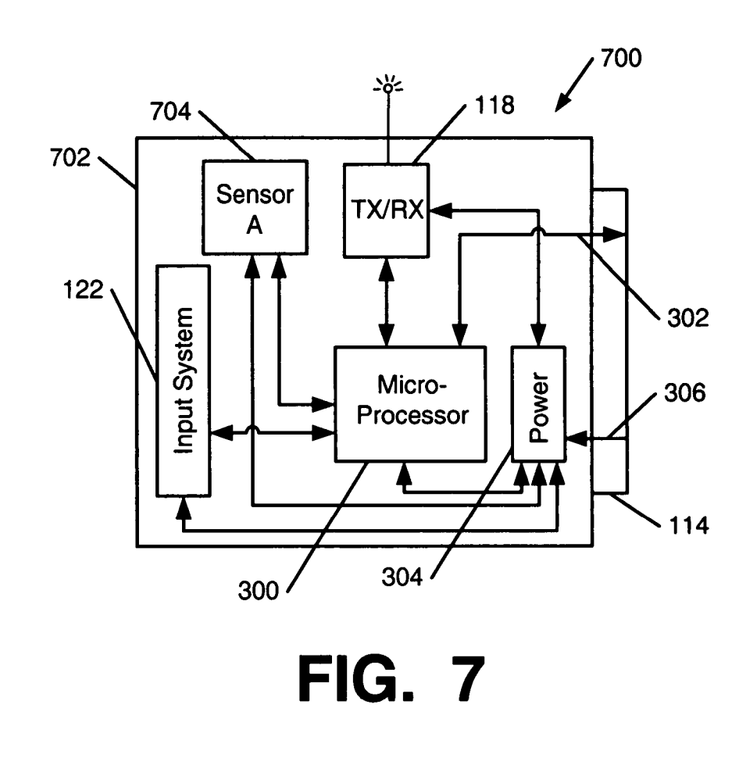
FIG. 7 illustrates a schematic diagram showing components provided in another example of an electronic interface device in accordance with this invention.

FIG. 7 illustrates another example of an electronic interface device 700 in accordance with at least some examples of this invention. This example device 700 is similar to the electronic interface device 112 shown in FIG. 3, including the connection system 114 (e.g., for physically connecting to a display device (not shown)), input system 122, microprocessor 300, data output connection pin(s) or wire(s) 302, power supply 304, and power supply connection pin(s) or wire(s) 306. All or some of these elements may be mounted in or on a common housing member 702, on a common board, and/or otherwise operatively connected or associated with one another. The device 700 differs from that shown in FIG. 3 in that the device 700 of FIG. 7 includes an athletic performance monitoring sensor 704 directly on board the electronic interface device 700. The sensor 704 may sense any desired type of physical or physiological data associated with an athletic performance, such as step count data (e.g., for pedometer type speed and/or distance monitoring), direction data (e.g., via a compass, etc.), pulse rate data, GPS data, etc. By providing the sensor 704 directly on board and/or otherwise as part of the interface element 700, the separate external sensing element and wireless data transmission and/or reception systems (or other external data transmission or reception capability) may be eliminated from the overall athletic performance monitoring system (as shown in FIG. 7, the sensing element 704 may be directly wired, hardwired, or otherwise in communication with the processing system 300 included with the interface element 700).

Alternatively or additionally, if desired, as shown in FIG. 7, the interface element 700 still may be provided with data reception system 118, e.g., to enable communication with other sensors (such as additional athletic performance sensors), external data sources, computers, networks, or other processing systems, and/or other separate devices or systems, e.g., to allow data input. Such systems 700 have the flexibility to receive data from a variety of different sources including at least one directly on board the interface element 700.

Figure 8:
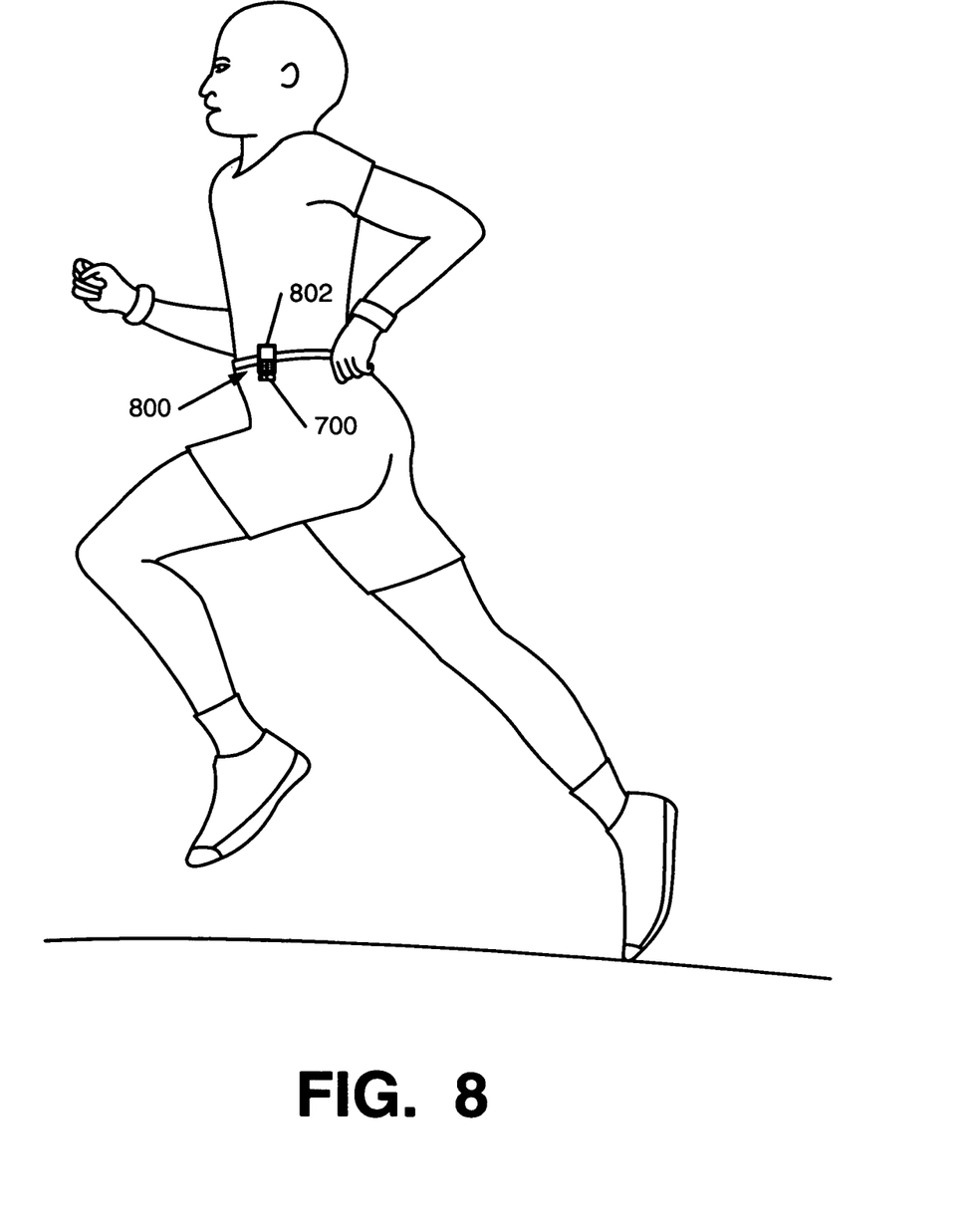
FIG. 8 illustrates an example system and an example environment in which various aspects and features of the electronic interface device of FIG. 7 may be used.

FIG. 8 illustrates an example arrangement and/or environment in which the system of FIG. 7 may be used. As shown in FIG. 8, the athletic performance monitoring system 800 of this example includes the electronic interface device 700 connected to a display device 802, such as a conventional cellular telephone or PDA. The combined system 800 then is attached to the user's apparel (e.g., clipped to a belt or waist band), and the user begins the athletic performance. During the performance, the sensor in the interface device 700 senses the athletic performance data (e.g., an accelerometer or other device that senses step count information), and this data then may be utilized to provide pedometer type speed and/or distance information that is then displayed on the display screen of display device 802. In this manner, it is not necessary for a user's footwear, clothing, or equipment to be separately equipped with a sensing device or module that communicates wirelessly or otherwise with an electronic interface device for providing input data to a display device. Of course, as noted above, any type of data may be sensed and/or displayed without departing from this invention.

Figure 9:
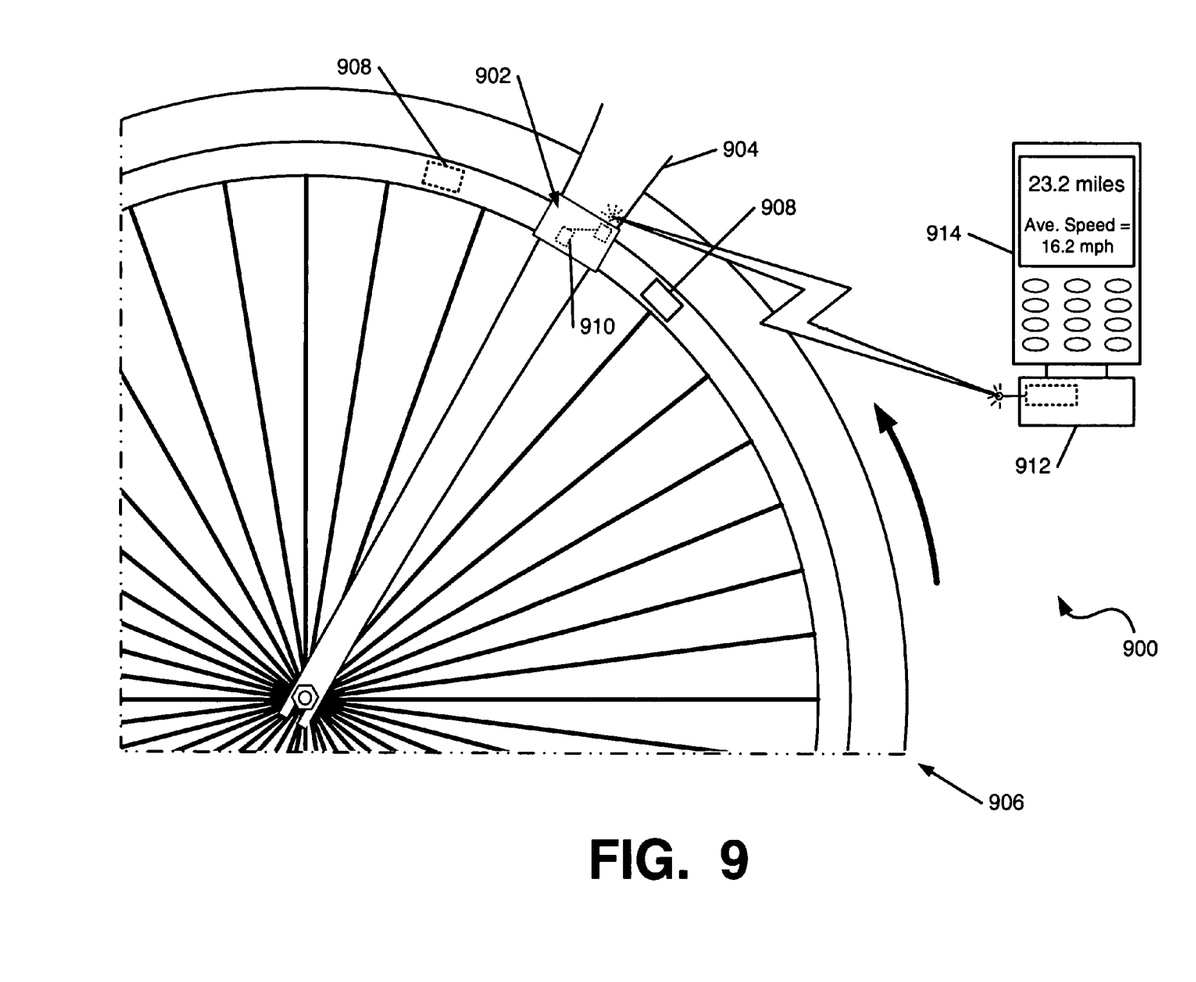
FIG. 9 illustrates an example of an athletic performance monitoring system in accordance with this invention in which the athletic performance data collection system is mounted on a piece of athletic equipment.

The specific example systems described above have related primarily to systems in which the various portions thereof (e.g., the sensing system, the electronic interface device and/or the display device) are attached to and/or integrated with various elements to be directly carried by the user in use. Systems and methods in accordance with at least some examples of this invention, however, are not limited to personally carried articles, such as personally carried sensors. FIG. 9 illustrates an example system 900 in which one or more sensing devices 902 are located or provided on an article of athletic equipment. More specifically, in the example illustrated in FIG. 9, a sensing device 902 is mounted to the fork 904 of a bicycle or other wheel 906. In this example structure 900, the wheel 906 includes a magnet source, a light or other radiation source, or other element 908 (e.g., mounted on the tire rim), and this source 908 is detected by a corresponding sensor 910 provided as part of the sensing device 902 as the wheel 906 turns. The number of times the source 908 passes the sensor 910 may be converted to speed and/or distance data, and this information (or the raw number of wheel revolutions) can be supplied to an electronic interface device 912 (e.g., wirelessly or otherwise), for processing, storage, and/or display on an electronic display device 914, such as a display screen of a cellular telephone, PDA, watch, etc. Of course, any type of data may be measured and any desired type of information may be displayed on display device 914 without departing from this invention. The display device may be carried by the user, mounted on the equipment (e.g., on the bicycle's handle bars), and/or otherwise made available to the user.

Of course, sensing devices of various types may be provided on a wide variety of different types of equipment (e.g., athletic equipment) and their sensed data (or data derived therefrom) may be forwarded to electronic interface devices in accordance with still additional examples of this invention. Examples of types of equipment that may have such sensors include, but are not limited to: pieces of athletic equipment that are swung, such as baseball or softball bats, golf clubs, cricket bats, tennis rackets, hockey sticks, and the like (e.g., to measure and display swing speed, projectile launch speed, angle, or direction, and/or other swing and/or projectile interaction characteristics, etc.); balls; baseball gloves; hockey equipment; impact-attenuation devices, such as knee pads and other padding equipment; boxing equipment; rowing or kayaking equipment; skiing equipment; etc.

III. Conclusion

While the invention has been described with respect to specific examples including presently preferred modes of carrying out the invention, those skilled in the art will appreciate that there are numerous variations and permutations of the above described systems and methods. For example various aspects of the invention may be used in different combinations and various different subcombinations of aspects of the invention may be used together in a single system or method without departing from the invention. Also, various elements, components, and/or steps described above may be changed, changed in order, omitted, and/or additional elements, components, and/or steps may be added without departing from this invention. Thus, the invention should be construed broadly as set forth in the appended claims.

I claim:

1. An athletic performance monitoring system, comprising:
    a sensing device configured to sense physical or physiological data associated with an athletic performance;
    a data transfer system in communication with the sensing device configured to transmit athletic performance data, wherein the athletic performance data includes a metric associated with an athlete's performance based on at least some portion of the physical or physiological data or data derived, at least in part, from at least some portion of the physical or physiological data; and
    an electronic interface device as a separate physical component from the sensing device and from the data transfer system, wherein the electronic interface device physically plugs into the portable electronic device and is carried along with the portable electronic device during the athletic performance, the electronic interface device having a first housing, the first housing including:
        an input in wireless communication with the data transfer system configured to receive the performance data; and
        an output having at least one connection element configured to releasably directly plug into and physically contact an input port of the portable electronic device during the athletic performance, wherein the output system is adapted to provide display data including at least a portion of the athletic performance data to the portable electronic device via the at least one connection element, wherein the display data includes real time athletic performance data, and wherein the portable electronic device is configured to attach to a user's article of clothing, article of footwear, or body during the athletic performance.

2. An athletic performance monitoring system according to claim 1, further comprising:
    a second housing configured to hold the sensing device and the data transfer system as a single component separate from the physical component of the electronic interface device.

3. An athletic performance monitoring system according to claim 2, wherein the second housing includes a device configured to attach to the user's article of clothing, article of footwear, or body or to a piece of athletic equipment.

4. An athletic performance monitoring system according to claim 1, wherein the electronic interface device further includes a processing system configured to receive the performance data via the input and configured to supply the display data to the output.

5. An athletic performance monitoring system according to claim 1, wherein the input includes a wireless data receiving system and the data transfer system includes a wireless data transmission system in communication with the wireless data receiving system.

6. An athletic performance monitoring system according to claim 1,
    wherein the sensing device is mounted in or on the user's article of footwear.

7. An athletic performance monitoring system according to claim 1,
    wherein the sensing device is mounted in or on the user's article of clothing.

8. An athletic performance monitoring system according to claim 1, further comprising:
    a piece of athletic equipment, wherein the sensing device is mounted in or on the piece of athletic equipment.

9. An athletic performance monitoring system according to claim 1, wherein the sensing device detects information relating to at least one member selected from the group consisting of: user speed data; user distance data; GPS data; altitude data; route data; user step count data; contact surface impact force data; ambient temperature data; ambient humidity data; barometric pressure data; sole member compression data; and jump height data.

10. An athletic performance monitoring system according to claim 1, wherein the sensing device detects information relating to at least one member selected from the group consisting of: pulse rate data; heart rate data; blood pressure data; body temperature data; hydration level data; air intake rate or volume data; air expel rate or volume data; EKG data; and EEG data.

11. An athletic performance monitoring system according to claim 1, wherein the portable electronic device is configured to control operations of the sensing device.

12. An athletic performance monitoring system according to claim 1, wherein the portable electronic device is configured to control operations of the data transfer system.

13. The athletic performance monitoring system of claim 1, wherein a signal received by the electronic interface device from the sensing device is processed, by the electronic interface device, to format the data for display on the portable electronic device.

14. An athletic performance monitoring system, comprising:
    a sensing device configured to sense physical or physiological data associated with an athletic performance;
    an electronic interface device as a separate physical component from the sensing device, the electronic interface device configured to receive athletic performance data from the sensing device, wherein the athletic performance data includes a metric associated with an athlete's performance, the electronic interface device physically plugs into a portable display device and is carried along with the portable display device during the athletic performance, and wherein the electronic interface device includes a first housing, the first housing including:

an input in wireless communication with and adapted to receive the performance data from the sensing device; and an output having at least one connection element configured to releasably and physically plug directly into and contact the portable display device during the athletic performance; and wherein when the portable display device is mated to the at least one connection element, the output is configured to provide display data including the athletic performance data to the portable display device, and wherein the display data includes real time athletic performance data displayed on the portable display device based on at least some portion of the performance data or data derived, at least in part, from at least some portion of the performance data, wherein the portable display device is configured to be attached to a user's article of clothing, article of footwear, or body during the athletic performance.

15. An athletic performance monitoring system according to claim 14, further comprising:
a data transfer system; and
a second housing configured to hold the sensing device and the data transfer system as a single component separate from the physical component of the electronic interface device.

16. An athletic performance monitoring system according to claim 15, wherein the second housing includes a device configured to attach to the user's article of clothing, article of footwear, or body or to a piece of athletic equipment.

17. An athletic performance monitoring system according to claim 15, wherein the data transfer system includes a wireless data transmitting device and the input includes a wireless data receiving device in communication with the wireless data transmitting device.

18. An athletic performance monitoring system according to claim 14, wherein the sensing device is mounted in or on the user's article of footwear.

19. An athletic performance monitoring system according to claim 14, wherein the sensing device is mounted in or on the user's article of clothing.

20. An athletic performance monitoring system according to claim 14, further comprising:
a piece of athletic equipment, wherein the sensing device is mounted in or on the piece of athletic equipment.

21. An athletic performance monitoring system according to claim 14, wherein the portable display device includes an audio/video display device.

22. An athletic performance monitoring system according to claim 14, wherein the portable display device includes a cellular telephone.

23. An athletic performance monitoring system according to claim 14, wherein the portable display device includes an MP3 player.

24. An athletic performance monitoring system according to claim 14, wherein the portable display device includes an off the shelf audio or video communication device.

25. An athletic performance monitoring system according to claim 14, wherein the portable display device is configured to control operations of the sensing device.

26. An athletic performance monitoring system according to claim 14, wherein the portable display device is configured to control operations of the data transfer system.

27. The athletic performance monitoring system of claim 14, wherein the received athletic performance data is processed by the electronic interface device to format the received athletic performance data for display on the portable display device.

* * * * *